(12) United States Patent
Custodero et al.

(10) Patent No.: US 6,975,396 B2
(45) Date of Patent: Dec. 13, 2005

(54) REINFORCING ALUMINUM-BASED FILLER AND RUBBER COMPOSITION COMPRISING SUCH A FILLER

(75) Inventors: Emmanuel Custodero, Chamalieres (FR); Laure Simonot, Clermont-Ferrand (FR); Jean-Claude Tardivat, Clermont-Ferrand (FR)

(73) Assignee: Compagnie Generale des Establissements Michelin-Michelin & Cie, Cleremont-Ferrand (FR)

( * ) Notice: Subject to any disclaimer, the term of this patent is extended or adjusted under 35 U.S.C. 154(b) by 323 days.

(21) Appl. No.: 10/426,359

(22) Filed: Apr. 30, 2003

(65) Prior Publication Data

US 2003/0202923 A1 Oct. 30, 2003

Related U.S. Application Data

(62) Division of application No. 09/583,653, filed on May 30, 2000, now Pat. No. 6,610,261, which is a continuation of application No. PCT/EP98/07680, filed on Nov. 27, 1998.

(30) Foreign Application Priority Data

Nov. 28, 1997 (FR) .............................. 97 15128

(51) Int. Cl.$^7$ ............................... G01N 15/02
(52) U.S. Cl. ...................... 356/336; 356/338
(58) Field of Search ................ 356/335–343, 356/440, 39, 73; 73/54.41; 250/574

(56) References Cited

U.S. PATENT DOCUMENTS

| | | |
|---|---|---|
| 3,268,295 A | 10/1966 | Armburst, Jr. |
| 3,842,111 A | 10/1974 | Meyer-Simon et al. |
| 3,873,489 A | 3/1975 | Thurn et al. |
| 3,978,103 A | 8/1976 | Meyer-Simon et al. |
| 3,997,581 A | 12/1976 | Pletka et al. |

(Continued)

FOREIGN PATENT DOCUMENTS

| | | |
|---|---|---|
| DE | 830944 | 1/1952 |
| EP | 0465205 | 1/1992 |
| EP | 0501227 | 9/1992 |
| EP | 0559529 | 9/1993 |
| EP | 0697432 | 2/1996 |
| EP | 0735088 | 10/1996 |
| EP | 0807603 | 11/1997 |
| EP | 0810258 | 12/1997 |
| FR | 2713773 | 6/1995 |
| GB | 2203542 | 10/1988 |

OTHER PUBLICATIONS

International Search Report for International Application No. PCT/EP 98/07680, Jul. 23, 1999.

(Continued)

*Primary Examiner*—Hoa Q. Pham
(74) *Attorney, Agent, or Firm*—Fitzpatrick, Cella, Harper & Scinto

(57) ABSTRACT

A reinforcing aluminum-based filler which can be used for reinforcing diene rubber compositions intended for the manufacture of tires, comprising an aluminum (oxide) hydroxide corresponding, with the exception of any impurities and the water of hydration, to the general formula (a and b being real numbers):

$$Al(OH)_aO_b, \text{ with } 0 < a \leq 3 \text{ and } b = (3-a)/2, \qquad (I)$$

the specific BET surface area of which is between 30 and 400 m$^2$/g, the average particle size (by mass) $d_w$ of which is between 20 and 400 nm and the disagglomeration rate, $\alpha$, of which, measured via an ultrasound disagglomeration test at 100% power of a 600-watt ultrasonic probe, is greater than $5 \times 10^{-3} \ \mu m^{-1}/s$ is provided. A rubber composition suitable for the manufacture of tires comprising said aluminum-based filler as reinforcing filler.

8 Claims, 4 Drawing Sheets

U.S. PATENT DOCUMENTS

| | | | |
|---|---|---|---|
| 4,002,594 A | | 1/1977 | Fetterman |
| 4,299,489 A | * | 11/1981 | Thery et al. ................ 356/336 |
| 4,514,511 A | | 4/1985 | Jacques et al. |
| 4,606,631 A | * | 8/1986 | Anno et al. .................... 356/39 |
| 5,305,072 A | | 4/1994 | Sawada et al. |
| 5,403,570 A | | 4/1995 | Chevallier et al. |
| 5,580,919 A | | 12/1996 | Agostini et al. |
| 5,583,245 A | | 12/1996 | Parker et al. |
| 5,663,396 A | | 9/1997 | Musleve et al. |
| 5,665,605 A | | 9/1997 | Coakley et al. |
| 5,684,171 A | | 11/1997 | Wideman et al. |
| 5,684,172 A | | 11/1997 | Wideman et al. |
| 5,696,197 A | | 12/1997 | Smith et al. |
| 5,800,922 A | | 9/1998 | Anderson et al. |
| 6,610,261 B1 | * | 8/2003 | Custodero et al. .......... 423/127 |
| 6,770,367 B1 | * | 8/2004 | Custodero et al. .......... 428/403 |
| 6,835,769 B2 | * | 12/2004 | Custodero et al. .......... 524/497 |
| 2002/0004549 A1 | * | 1/2002 | Custodero et al. .......... 524/497 |
| 2003/0202923 A1 | * | 10/2003 | Custodero et al. .......... 423/127 |
| 2004/0030017 A1 | * | 2/2004 | Simonot et al. ............ 524/424 |
| 2005/0016650 A1 | * | 1/2005 | Durel et al. ............. 152/209.1 |
| 2005/0016651 A1 | * | 1/2005 | Durel et al. ............. 152/209.1 |

OTHER PUBLICATIONS

Brunauer, Emmet and Teller described in "The Journal of the American Chemical Society", vol. 60, p. 309–319, Feb. 1938, corresponding to Standard AFNOR–NF–T45–007 (Nov. 1987).

Plastics, Rubber and Composites Processing and Applications, vol. 25, No. 7, p. 327–331 (1996).

Rubber Chemistry and Technology, vol. 69, p. 325–346 (1996).

* cited by examiner

REINFORCING ALUMINUM-BASED FILLER AND RUBBER COMPOSITION COMPRISING SUCH A FILLER

The present application is a divisional application of U.S. Ser. No. 09/583,653, filed May 30, 2000, now U.S. Pat. No. 6,610,261 which is a continuation of PCT/EP98/07680, filed Nov. 27, 1998, now WO 99/28376.

BACKGROUND OF INVENTION

The present invention relates to diene rubber compositions reinforced with white fillers, which can be used for the manufacture of tires or semi-finished products for tires and, in particular, tire treads.

The invention pertains to an aluminum based reinforcing white filler and to diene rubber compositions containing this filler.

In order to reduce fuel consumption and pollution emitted by motor vehicles, major attempts have been made by tire designers to obtain tires having all of the following characterisics: very low rolling resistance, improved grip both on dry ground and on wet or snow-covered ground, and very good wear resistance.

Numerous solutions have thus been proposed to lower the rolling resistance and to improve the grip of tires, but these have generally resulted in a very great decline in the wear resistance.

It is well known that the incorporation of conventional white fillers, such as silica ($SiO_2$), alumina ($Al_2O_3$), titanium oxide ($TiO_2$), chalk, talc, clays such as bentonite or kaolin for example, in rubber compositions used for the manufacture of tires and, in particular, of treads, results in a reduction in the rolling resistance and an improvement in grip to wet, snow-covered or icy ground. However, it also results in an unacceptable decline in the wear resistance because these conventional white fillers do not have sufficient reinforcement ability with respect to such rubber compositions. For this reason, these white fillers are generally referred to as non-reinforcing fillers, or alternatively inert fillers.

One effective solution to this problem was described in Patent Application EP-A-0 501 227, which discloses a sulphur-vulcanizable diene rubber composition obtained by thermo-mechanical working of a conjugated diene copolymer and an aromatic vinyl compound prepared by solution polymerization. This composition also comprises a special highly dispersible precipitated silica as reinforcing white filler. This composition makes it possible to manufacture a tire having substantially improved rolling resistance, without affecting the other properties, in particular those of grip, endurance and, above all, wear resistance.

Other compositions having such an excellent balance between several contradictory properties would be of great interest to tire manufacturers, who would thus have different choices available to them. Furthermore, the improvement in wear resistance thus obtained might possibly be converted into a lowering of the rolling resistance by reducing the thickness of the tread. It would thus be conceivable to construct tires having an unchanged life, but which are lighter and therefore consume less energy.

During the course of their research, the Inventors have discovered a novel reinforcing white aluminum-based filler, based on an aluminum compound, which unexpectedly makes it possible to obtain a level of reinforcement at least equal to that obtained with highly dispersible silicas.

SUMMARY OF THE INVENTION

The invention relates to a reinforcing aluminum-based filler which can be used for reinforcing diene rubber compositions intended for the manufacture of tires. The filler comprises an aluminum (oxide-)hydroxide corresponding, with the exception of any impurities and the water of hydration, to the general Formula I (a and b being real numbers):

$$Al(OH)_aO_b, \text{ where: } 0 < a \leq 3 \text{ and } b=(3-a)/2, \quad (I)$$

the specific BET surface area of which is between 30 and 400 m²/g, the average particle size (by mass) $d_w$ of which is between 20 and 400 nm and the disagglomeration rate, α, of which, measured via the ultrasound disagglomeration test, at 100% power of a 600-watt ultrasonic probe, is greater than $5 \times 10^{-3}$ μm⁻¹/s.

Aluminum oxides or hydroxides have already been described as various additives in rubber compositions for tires. By way of example, Patent Application EP-A-0 697 432 describes the use of various inorganic powders of Al, Mg, Ti, Ca, or of oxides or hydroxides of these elements, in particular alumina ($Al_2O_3$) or aluminum tri-hydroxide $Al(OH)_3$, with the aim of improving braking and grip performance on wet ground. However, these inert fillers have neither the function nor the abilities of reinforcing fillers in the rubber compositions described. The compositions are reinforced in conventional manner by carbon black, with which silica and a coupling agent for this silica may possibly be associated.

Thus, to the Inventors' knowledge, the prior art neither describes nor suggests the present aluminum-based filler which, because of its characteristics, is capable on its own of reinforcing diene rubber compositions useful in the manufacture of tires. Such compositions have substantially the advantageous properties of the silica-based compositions described in the above-mentioned Patent Application EP-A-0 501 227.

A second subject of the invention relates to a process for obtaining an aluminum-based filler according to the invention, comprising:

(i) reacting an aqueous solution of a Brönsted base under stirring with an aqueous solution of an aluminum salt in order to precipitate the aluminum salt in a suspension of aluminum hydroxide;

(ii) filtering the suspension thus obtained and washing it with water;

(iii) drying the filtrate thus obtained with a drying means suitable for limiting the agglomeration of the particles of hydroxide upon elimination of the water; and (iv) then heat-treating the compound thus obtained so as to obtain an aluminum (oxide-)hydroxide.

Another subject of the invention relates to a sulphur-vulcanizable rubber composition which can be used for the manufacture of tires, comprising at least one diene elastomer, a reinforcing white filler and a coupling agent linking the reinforcing filler and the elastomer, wherein the white filler is formed in its entirety or in part by an aluminum-based filler according to the invention.

Another subject of the invention is a process for reinforcing a diene rubber composition which can be used for the manufacture of tires, comprising incorporating an aluminum-based filler according to the invention into the composition by mixing in an internal mixer, before introducing the vulcanization system.

Another subject of the invention is the use, as reinforcing filler, of an aluminum-based filler according to the invention in a diene rubber composition which can be used for manufacturing tires.

Another subject of the invention is the use of a rubber composition according to the invention for the manufacture of rubber articles, in particular tires or semi-finished products, these semi-finished articles being selected from the group consisting of treads, underlayers intended, for example, to be positioned beneath these treads, crown plies, sidewalls, carcass plies, beads, protectors, inner tubes and airtight internal rubbers for tubeless tires. The invention relates more particularly to the use of such a rubber composition for the manufacture of the sidewalls or treads, owing to its good hysteretic properties.

The composition according to the invention is particularly suitable for the construction of treads for tires intended to be fitted on passenger vehicles, vans, two-wheelers and heavy vehicles, aircraft, construction, agricultural or handling machinery, wherein such treads are usable in the manufacture of new tires or for recapping worn tires.

The subject of the invention is also such tires and rubber articles themselves when they comprise a rubber composition according to the invention.

BRIEF DESCRIPTION OF THE DRAWINGS

The invention and its advantages will be more readily understood in light of the detailed description, the examples which follow and the drawings in which.

DETAILED DESCRIPTION

I. Measurements and Tests Used

I-1. Characterization of the Aluminum-based Fillers

Figure 1:
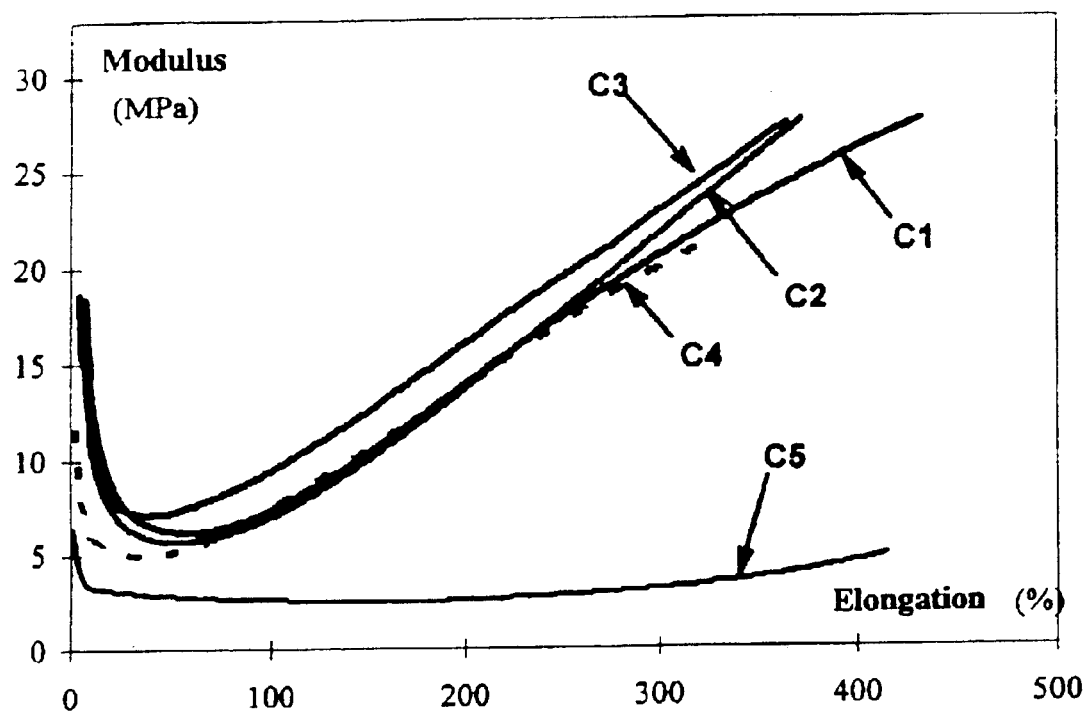
FIGS. 1 and 2 depict curves of the variation of modulus as a function of elongation for different diene rubber compositions, whether or not in accordance with the invention.

The aluminum-based fillers of the invention, in the form of finely divided powder, are characterized as indicated hereafter.

a) BET Specific Surface Area:

The BET specific surface area is determined in known manner, in accordance with the method of Brunauer, Emmet and Teller described in "The Journal of the American Chemical Society", vol. 60, page 309, February 1938, corresponding to Standard AFNOR-NF-T45-007 (November 1987).

b) Average Size of the Particles $d_w$:

The average size (by mass) of the particles, $d_w$, is measured after dispersion of the filler by ultrasound disagglomeration with the analysis being carried out in an aqueous solution of 0.6% by weight sodium hexametaphosphate. For better stability of the suspension, in the case of BET surface areas greater than 200 m$^2$/g, a concentration of 1% by weight is preferably used.

The term "particle" as used in the present application is understood to mean "aggregate", and not that of a possible elementary particle which may form part of this aggregate ("aggregate" is understood, in known manner, to mean a non-splittable unit of elementary particles, produced during synthesis of the filler).

Measurements are carried out using a centrifugal X-ray detection sedimentometer, type "XDC" ("X-ray Disk Centrifuge"), sold by Brookhaven Instruments, in accordance with the following method of operation: a suspension of 3.2 g of a sample of filler to be analyzed in 40 ml of water containing 6 g/l of sodium hexametaphosphate as surfactant (preferably 10 g/l in the case of a BET>200 m$^2$/g) is produced by action over 8 minutes at 60% power (60% of the maximum position of the output control) of a 1500-watt ultrasonic probe (Vibracell ¾ inch ultrasound generator sold by Bioblock); after ultrasound generation, 15 ml of the suspension is introduced into the rotating disc. After sedimentation for 120 minutes, the mass distribution of the particle sizes and the average size by mass $d_w$ are calculated by the software of the "XDC" sedimentometer ($d_w = \Sigma(n_i d_i^5)/\Sigma(n_i d_i^4)$ where $n_i$=number of objects of the size class $d_i$).

c) Disagglomeration Rate α:

The disagglomeration rate, α, is measured using the "ultrasound disagglomeration test", at 100% power of a 600-watt probe. This test makes it possible to continuously measure the evolution of the average size (in volume) of the agglomerates of particles during ultrasound generation, as indicated below.

The setup used is formed by a laser granulometer ("Mastersizer S", sold by Malvern Instruments) and its preparer ("Malvern Small Sample Unit MSX1"), between which there has been inserted a continuous-flow treatment cell (Bioblock M72410) provided with an ultrasonic probe (600-watt ultrasound generator Vibracell ½ inch sold by Bioblock). A small quantity (150 mg) of filler to be analyzed is introduced into the preparer with 160 ml of water, with the rate of circulation being set to its maximum. At least three consecutive measurements are made (without ultrasound generation) to determine the initial mean diameter (by volume) of the agglomerates, referred to as $d_v[0]$, in accordance with the known Fraunhofer calculation method (Malvern 3$$D calculation matrix). The ultrasound generation is then set at a power of 100% ("tip amplitude" in maximum position) and the evolution of the mean diameter by volume $d_v[t]$ as a function of the time "t" is monitored for about 8 minutes with one measurement approximately every 10 seconds. After an induction period of about 3 minutes, it was noted that the reciprocal of the mean diameter in volume $1/d_v[t]$ varies linearly with the time "t" (steady state conditions of disagglomeration). The disagglomeration rate α is calculated by linear regression of the curve of evolution of $1/d_v[t]$ as a function of the time "t", within the zone of steady state conditions of disagglomeration. It is expressed in $\mu m^{-1}$/s.

By way of example and as reference, the ultrasound disagglomeration test above, applied to a control silica well-known to the person skilled in the art for its very good dispersibility (silica sold by Rhône-Poulenc under the reference Zeosil 1165MP), results in a disagglomeration rate, $\alpha_0$, of approximately $7.5 \times 10^{-3}$ $\mu m^{-1}$/s.

I-2. Characterization of the Rubber Compositions

The rubber compositions are characterized, before and after curing, as indicated below.

a) Mooney Plasticity:

An oscillating consistometer such as described in standard AFNOR-NF-T43-005 (November 1980) is used. The Mooney plasticity is measured in accordance with the following principle: the uncured mix is molded in a cylindrical enclosure heated to 100° C. After preheating for one minute, the rotor turns within the test piece at 2 rpm, and the torque used for maintaining this movement is measured after four minutes' rotation. The Mooney plasticity (MS 1+4) is expressed in "Mooney units" (MU).

b) Tensile Tests:

These tests make it possible to determine the elasticity stresses and the breaking properties. Unless indicated otherwise, they are carried out in accordance with the standard AFNOR-NF-T46-002 of September 1988.

The secant moduli at 10% elongation (M10), 100% elongation (M100) and 300% elongation (M300) are measured. These moduli are calculated reduced to the real section of the test piece and, unless indicated otherwise, are measured in a second elongation (i.e. after an accommodation cycle). All these tensile measurements are carried out under normal conditions of temperature and humidity in accordance with the standard AFNOR-NF-T40-101 (December 1979). Processing the recorded tensile data also makes it possible to trace the curve of the modulus as a function of elongation (see FIGS. 1 and 2). The modulus used here being the secant modulus measured in a first elongation (i.e. without an accommodation cycle), calculated reduced to the real cross-section of the test piece.

c) Hysteresis Losses:

The hysteresis losses (HL) are measured by rebound at 60° C. at the sixth impact, and are expressed in % in accordance with the following equation:

$HL$ (%)=100[$(W_0-W_1)/W_0$], where $W_0$=energy supplied; $W_1$=energy restored.

d) Dynamic Properties:

The dynamic properties, referred to as $\Delta G^*$ and $\tan(\delta)_{max}$, measured as a function of the deformation, are carried out at 10 Hertz with a peak-to-peak deformation of 0.15% to 50%. The non-linearity $\Delta G^*$ is the difference in the shear modulus between 0.15% and 50% deformation, expressed in MPa. The hysteresis is expressed by the measurement of $\tan(\delta)_{max}$ which corresponds to the maximum of $\tan(\delta)$.

e) "Bound Rubber" Test:

The so-called "bound rubber" test makes it possible to determine the proportion of elastomer, in a non-vulcanized composition, which is intimately associated with the reinforcing filler such that this proportion of elastomer is insoluble in the usual organic solvents. The determination of this insoluble proportion of rubber, fixed by the reinforcing filler during mixing, gives a quantitative indication of the reinforcing activity of the filler in the rubber composition. Such a method has been described, for example, in standard NF-T-45-114 (June 1989) applied to the determination of the amount of elastomer bound to the carbon black.

This test, which is well-known to the person skilled in the art for characterizing the quality of reinforcement provided by the reinforcing filler, has been described, for example, in the following documents: *Plastics, Rubber and Composites Processing and Applications*, Vol. 25, No. 7, p. 327 (1996); *Rubber Chemistry and Technology*, Vol. 69, p. 325 (1996).

In the present case, the amount of elastomer which cannot be extracted with toluene is measured, after swelling a sample of rubber composition (typically 300–350 mg) in this solvent (for example in 80–100 cm³ of toluene for 15 days), followed by a 24-hour drying step at 100° C., in vacuo before weighting the sample of rubber composition thus treated. Preferably, the swelling stage is carried out at ambient temperature (approximately 20° C.) protected from light, in which the solvent (toluene) is changed once, for example after swelling for five days'. The amount of "bound rubber" (% by weight) is calculated in known manner by the difference between the initial weight and the final weight of the sample of rubber composition, after allowing for and eliminating, in the calculation, the fraction of the components which are insoluble by nature, other than the elastomer, which are initially present in the rubber composition.

II. Conditions of Carrying Out the Invention

In addition to the usual additives or those capable of being used in a sulphur-vulcanizable rubber composition which can be used for the manufacture of tires, the compositions according to the invention comprise, as base constituents, (i) at least one diene elastomer, (ii) a reinforcing white filler and (iii) a coupling agent between the white filler and the elastomer, wherein white filler is in its entirety or in part an aluminum-based filler according to the invention.

II-1. Diene Elastomer

"Diene" elastomer or rubber is understood to mean, in known manner, an elastomer resulting at least in part (i.e. a homopolymer or a copolymer) from diene monomers (monomers bearing two double carbon-carbon bonds, whether conjugated or not).

Generally, "essentially unsaturated" diene elastomer is understood to mean a diene elastomer resulting at least in part from conjugated diene monomers having a content of members or units of diene origin (conjugated dienes) which is greater than 15% (mole %).

Thus, for example, diene elastomers such as butyl rubbers or copolymers of dienes and of alpha-olefins of the EPDM type do not fall within the preceding definition, and may in particular be described as "essentially saturated" diene elastomers (low or very low content of units of diene origin which is always less than 15%).

Within the category of "essentially unsaturated" diene elastomers, "highly unsaturated" diene elastomer is understood to mean a diene elastomer having a content of units of diene origin (conjugated dienes) which is greater than 50%.

These definitions being given, the following are understood to be meant by diene elastomer capable of being used in the compositions according to the invention:

(a) any homopolymer obtained by polymerization of a conjugated diene monomer having 4 to 12 carbon atoms;

(b) any copolymer obtained by copolymerization of one or more dienes conjugated together or with one or more vinyl aromatic compounds having 8 to 20 carbon atoms;

(c) any ternary copolymer obtained by copolymerization of ethylene, and an α-olefin having 3 to 6 carbon atoms with a non-conjugated diene monomer having 6 to 12 carbon atoms, such as, for example, the elastomers obtained from ethylene, from propylene with a non-conjugated diene monomer of the aforementioned type, including inter alia 1,4-hexadiene, ethylidene norbornene or icyclopentadiene;

(d) any copolymer of isobutene and isoprene (butyl rubber), as well as halogenated, in particular chlorinated or brominated, versions of this type of copolymer.

Although it applies to any type of diene elastomer, a person skilled in the tire art will understand that the present invention is used primarily with essentially unsaturated diene elastomers, in particular those of type (a) or (b) above.

Suitable conjugated dienes are, in particular, 1,3-butadiene, 2-methyl-1,3-butadiene, the 2,3-di($C_1$ to $C_5$ alkyl)-1,3-butadienes such as, for example, 2,3-dimethyl-1,3-butadiene, 2,3-diethyl-1,3-butadiene, 2-methyl-3-ethyl-1,3-butadiene, 2-methyl-3-isopropyl-1,3-butadiene, an aryl-1,3-butadiene, 1,3-pentadiene and 2,4-hexadiene.

Suitable vinyl aromatic compounds are, in particular, styrene, ortho-, meta- and para-methylstyrene, the commercial mixture "vinyl-toluene", para-tertiobutylstyrene, the methoxy-styrenes, the chloro-styrenes, vinyl mesitylene, divinyl benzene and vinyl naphthalene.

The copolymers comprise between 99% and 20% by weight of diene units and between 1% and 80% by weight of vinyl aromatic units. The elastomers may have any microstructure, which is a function of the polymerization conditions used, in particular of the presence or absence of a modifying and/or randomizing agent and the quantities of modifying and/or randomizing agent used. The elastomers may, for example, be block, statistical, sequenced or microsequenced elastomers, and may be prepared in dispersion or in solution.

Polybutadienes are preferred, particularly those having a 1,2 bond content of between 4% and 80% and those having a content of cis-1,4 bonds of more than 90%, polyisoprenes; butadiene-styrene copolymers, and in particular those having a styrene content of between 5% and 50% by weight and, more particularly, between 20% and 40% by weight, a 1,2 bond content of the butadiene part of between 4% and 65%, and a content of trans-1,4 bonds of between 20% and 80%; butadiene-isoprene copolymers, particularly those having an isoprene content of between 5% and 90% by weight and a glass transition temperature (Tg) of −40° C. to −80° C. and isoprene-styrene copolymers, particularly those having a styrene content of between 5% and 50% by weight and a Tg of between −25° C. and −50° C.

In the case of butadiene-styrene-isoprene copolymers, there are suitable in particular those having a styrene content of between 5% and 50% by weight and, more particularly, between 10% and 40%, an isoprene content of between 15% and 60% by weight, and more particularly between 20% and 50%, a butadiene content of between 5% and 50% by weight, and more particularly between 20% and 40%, a content of 1,2-units of the butadiene part of between 4% and 85%, a content of trans-1,4 units of the butadiene part of between 6% and 80%, a content of 1,2-plus 3,4-units of the isoprene part of between 5% and 70%, and a content of trans-1,4 units of the isoprene part of between 10% and 50%, and more generally any butadiene-styrene-isoprene copolymer having a Tg of between −20° C. and −70° C., and more generally any butadiene-styrene-isoprene copolymer having a Tg of between 20° C. and −70° C.

The elastomer may be coupled and/or starred or alternatively functionalized with a coupling and/or starring or functionalizing agent. The elastomer may also be natural rubber or a blend based on natural rubber with any synthetic elastomer, in particular a diene elasomer.

In particular, the diene elastomer of the composition of the invention is selected from among highly unsaturated diene elastomers which include polybutadienes, polyisoprenes or natural rubber, butadiene-styrene copolymers, butadiene-isoprene copolymers, isoprene-styrene copolymers, butadiene-styrene-isoprene copolymers, or a mixture of two or more of these elastomers.

When the composition of the invention is intended for a tread for a tire, the diene elastomer is preferably a butadiene-styrene copolymer prepared in solution having a styrene content of between 20% and 30% by weight, a content of vinyl bonds of the butadiene part of between 15% and 65%, a content of trans-1,4 bonds of between 20% and 75%, and a glass transition temperature Tg of between −20° C. and −55° C. This butadiene-styrene copolymer may also be used in a mixture with a polybutadiene having preferably more than 90% cis-1,4 bonds.

II-2. Reinforcing Filler

As indicated previously, the reinforcing aluminum-based filler of the invention comprises an aluminum (oxide-)hydroxide corresponding, with the exception of any impurities and the water of hydration, to the general Formula I (a and b being real numbers):

$$Al(OH)_aO_b \text{ where: } 0<a\leq 3 \text{ and } b=(3-a)/2, \quad (I)$$

the specific BET surface area of which is between 30 and 400 m$^2$/g, the average particle size (by mass) d$_w$ of which is between 20 and 400 nm and the disagglomeration rate, α, of which, measured via the ultrasound disagglomeration test, at 100% power of a 600-watt ultrasonic probe, is greater than $5\times10^{-3}$ μm$^{-1}$/s.

"Aluminum (oxide-)hydroxide" is understood to mean any hydroxide or oxide-hydroxide of aluminum corresponding to the general Formula (I) above, i.e., either an aluminum tri-hydroxide Al(OH)$_3$ (a=3), or an aluminum oxide-hydroxide (a<3), or a mixture of aluminum tri-hydroxides and/or oxide-hydroxides.

Formula (I) is given with the exception of any impurities and the water of hydration. It is understood that the aluminum (oxide-)hydroxides may comprise a certain proportion of bound water (corresponding formula: [Al(OH)$_a$O$_b$.n H$_2$O], with n varying for example from 1 to 3) or certain impurities resulting from the process used for manufacturing the filler.

According to a preferred embodiment of the invention, the aluminum-based filler is an oxide-hydroxide (a<3), also commonly referred to as oxyhydroxide. In the examples of set forth below it has been noted that, of the aluminum-based fillers according to the invention, the oxyhydroxides demonstrated reinforcement abilities even greater than those offered by the tri-hydroxides, when incorporated into diene rubber compositions intended for the manufacture of tires.

For these reasons, the aluminum oxyhydroxide of the invention more preferably satisfies the relationship: 0<a<2.

In order to be able to play an effective reinforcing role for the diene rubber compositions, i.e., to induce an improvement in their mechanical properties and thus be termed reinforcing fillers, the aluminum oxides-hydroxides must be in a finely divided state having all the characteristics of BET, of average size d$_w$ and of disagglomeration rate α set forth previously above.

Where the BET surface area is less than 30 m$^2$/g, the compositions have easier working (suitability for transformation or "processability") and a reduced hysteresis, but exhibit a decline in the breaking and wear resistance properties in the tire comprising such fillers; where the BET surface areas are greater than 400 m$^2$/g, working in the uncured state becomes more difficult (higher Mooney plasticity) and the dispersion of the filler is adversely affected as a result. For excessively large sizes where d$_w$ is greater than 400 nm, the particles act like defects which localize stresses and are harmful in terms of wear, where sizes d$_w$ are too small, i.e., less than 20 nm, on the other hand, working in the uncured state and the dispersion of the filler during this working are impaired.

For all the reasons set forth above, the BET surface area preferably is within a range from 50 to 350 m$^2$/g and the particle size d$_w$ preferably is within a range from 30 to 200 nm; more preferably the BET surface area is within a range from 70 to 300 m$^2$/g and the particle size d$_w$ is within a range from 50 to 150 nm.

The intrinsic dispersibility of a filler can be evaluated via the ultrasound disagglomeration test described in Section I above, by measuring the disagglomeration rate α. It has been noted that, for a rate α greater than $5\times10^{-3}$ μm$^{-1}$/s, the aluminum-based filler of the invention has satisfactory dispersibility, i.e., that few micronic agglomerates are observed by optical microscopy reflection on a section of a rubber composition prepared in accordance according to the art.

For even better dispersion of the aluminum-based filler in the diene rubber matrix, and therefore for optimum reinforcement, the disagglomeration rate α is preferably greater than $6 \times 10^{-3}$ $\mu m^{-1}/s$. This is particularly advantageous when the invention is used for manufacturing treads for tires which have both low rolling resistance and high wear resistance. More preferably still, the disagglomeration rate α is at least equal to $7.5 \times 10^{-3}$ $\mu m^{-1}/s$ (value $\alpha_0$ previously defined).

The filler of the invention has high surface reactivity, i.e. a high amount of surface functions (Al—OH) which are reactive with regard to a coupling agent (white filler/elastomer). This surface reactivity is particularly beneficial to the mechanical properties of the rubber compositions, to the reinforcement function performed by this filler.

The aluminum-based filler of the invention may be prepared by the following process.

First, an aqueous solution of a Brönsted base is reacted with an aqueous solution of an aluminum salt with stirring in order to precipitate the aluminum salt in a suspension of aluminum hydroxide. This first step is preferably carried out at a temperature higher than ambient temperature, for example at a temperature within a range from 25° C. to 50° C. approximately. Suitable Brönsted bases include sodium hydrogen carbonate, ammonium hydroxide, and ammonium carbonate, with the latter being preferred. The aluminum salt is, for example, aluminum sulphate or nitrate.

The suspension thus obtained is filtered and washed in water, with the filtration/washing operation being carried out once or several times.

The filtrate thus obtained is dried with a drying means suitable for limiting the agglomeration of the particles of hydroxide upon elimination of the water. The drying means which may be used are known to the person skilled in the art. For example, freeze-drying, spray-drying or supercritical conditions, or any other equivalent means which is suitable for avoiding excessive agglomeration, by capillary action, of the hydroxide particles upon the elimination of water.

Finally, the resultant compound is heat-treated so as to obtain an aluminum (oxide-)hydroxide. The temperature of this heat treatment is preferably between 100° C. and 700° C. Generally, the higher the temperature, the aluminum compound of Formula I "shifts" from hydroxide towards oxide (reduction of a and increase in b). Prolonged treatment at an excessively high treatment temperature, for example about 800° C. or more, results in obtaining a pure aluminum oxide (or alumina $Al_2O_3$) rather than an aluminum (oxide-)hydroxide. Thus the heat treatment temperature more preferably is within a range between 120° C. and 600° C., and even more preferably ranges from 150° C. to 550° C. The heat treatment may be carried out in air in any type of known oven. The duration of the heat treatment may vary to a great extent, according to the temperature selected and the type of oven used, for example from a few minutes to several hours.

The person skilled in the art will be able to adjust the different parameters above according to the particular conditions of implementation of the process and of the intended final compound, in light of the description and the examples which follow.

The white aluminum-based filler of the invention may be used alone or in association with another reinforcing filler, for example a reinforcing white filler such as silica. Preferably a highly dispersible precipitated silica is used as the second reinforcing white filler, in particular when the invention is used for the manufacture of treads for tires having low rolling resistance. Non-limiting examples of such preferred highly dispersible silicas, include silica Perkasil KS 430 from Akzo, the silica BV 3380 from Degussa, the silicas Zeosil 1165 MP and 1115 MP from Rhône-Poulenc, the silica Hi-Sil 2000 from PPG, and the silicas Zeopol 8741 or 8745 from Huber.

Preferably, in the compositions according to the invention, the aluminum-based filler of the invention constitutes the majority, i.e. more than 50% by weight, of the total reinforcing filler. The filler of the invention may advantageously constitute the entire reinforcing white filler.

The aluminum-based filler of the invention, alone or with a second reinforcing white filler, for example silica, may also be used in a blend, i.e. in a mixture, with carbon black. Suitable carbon blacks are all the reinforcing carbon blacks, in particular the blacks of the type HAF, ISAF and SAF, which are conventionally used in tires, and particularly in treads for tires. Non-limiting examples of such blacks, include the blacks of the series 100, 200 or 300 (ASTM grades), for example the blacks N115, N134, N234, N339, N347 and N375. The amount of carbon black in the total reinforcing filler (total white filler+black filler) may vary within wide limits, with the amount of carbon black preferably being less than the total amount of white filler.

Preferably, the amount of total reinforcing white filler in the compositions of the invention is in a range from 20 to 300 phr (parts per 100 parts by weight elastomer), more preferably from 30 to 150 phr, the optimum differing according to the intended applications. For example, the level of reinforcement expected for a bicycle tire, for example, is distinctly lower than that required for a tire for a passenger vehicle or for a utility vehicle such as a heavy vehicle.

II-3. Coupling Agent

When a reinforcing silica is used, it is well-known to the person skilled in the art a (silica/elastomer) coupling agent, also referred to as a bonding agent, the role of which is to produce a bond between the white filler and the elastomer, while facilitating the dispersion of this white filler within the elastomeric matrix.

The white aluminum-based filler of the invention also requires the use of such a coupling agent in order fully to perform its function of reinforcing filler in the rubber composition.

"Coupling" agent (white filler/elastomer) is more precisely understood to mean an agent capable of establishing a sufficient chemical and/or physical connection between the white filler and the elastomer, while facilitating the dispersion of the white filler within the elastomeric matrix. Such a coupling agent, which is at least bifunctional, has, for example, the general formula "Y-T-X", in which:

Y represents a functional group ("Y" function) which is capable of bonding physically and/or chemically with the white filler, such a bond being able to be established, for example, between a silicon atom of the coupling agent and the hydroxyl (OH) surface groups of the white filler (for example, surface silanols in the case of silica);

X represents a functional group ("X" function) which is capable of bonding physically and/or chemically with the elastomer, for example by means of a sulphur atom; and T represents a hydrocarbon group that links Y and X.

The coupling agents are not to be confused with simple agents for covering the white filler which, in known manner, comprise the Y function which is active with respect to the white filler, but are devoid of the X function which is active with respect to the elastomer.

Coupling agents, of variable effectiveness, have been described in a large number of documents, for example Patents U.S. Pat. No. 3,842,111, U.S. Pat. No. 3,873,489, U.S. Pat. No. 3,978,103, U.S. Pat. No. 3,997,581, U.S. Pat.

No. 4,002,594 and the more recent patents U.S. Pat. No. 5,580,919, U.S. Pat. No. 5,583,245, U.S. Pat. No. 5,663,396, U.S. Pat. No. 5,684,171, U.S. Pat. No. 5,684,172, U.S. Pat. No. 5,696,197, which describe such known compounds in detail.

In fact, any known coupling agent may be used to ensure, in diene rubber compositions which can be used for the manufacture of tires, effective bonding or coupling between the silica and diene elastomer. Such coupling agents include organosilanes, in particular polysulphurized alkoxysilanes, such as polysulphides, in particular tetrasulphides, bis(trialkoxy($C_1$–$C_4$)-silylpropyl), in particular bis(3-trimethoxysilylpropyl) or bis(3-triethoxysilylpropyl). In particular, bis(3-triethoxysilylpropyl) tetrasulphide, abbreviated TESPT, of the formula $[(C_2H_5O)_3Si(CH_2)_3S_2]_2$, sold, for example by Degussa under the name Si69, is used.

The person skilled in the art will be able to adjust the content of coupling agent in the compositions of the invention, according to the intended application, the nature of the polymer used, and the quantity of total reinforcing white filler used.

So as to allow for the differences in specific surface area and density of the reinforcing white fillers which may be used, as well as the molar masses of the coupling agents, it is preferable to determine the optimum amount of coupling agent, in moles per square meter of reinforcing white filler, for each white filler used. This optimum amount is calculated from the weight ratio [coupling agent/reinforcing white filler], the BET surface area of the filler and the molar mass of the coupling agent (referred to as M hereafter), according to the following equation:

$$(\text{moles/m}^2 \text{ white filler}) = [\text{coupling agent/white filler}](1/BET)(1/M)$$

Preferably, the quantity of coupling agent used in the compositions according to the invention lies between $10^{-7}$ and $10^{-5}$ moles per meter of total reinforcing white filler, i.e. per square meter of aluminum-based filler according to the invention when the latter constitutes the sole reinforcing white filler present. More preferably, the amount of coupling agent comprises between $5 \times 10^{-7}$ and $5 \times 10^{-6}$ moles per square meter of total reinforcing white filler.

II-4. Various Additives

The compositions according to the invention contain, in addition to the compounds already described, all or part of the constituents usually used in diene rubber compositions intended for the manufacture of tires, such as plasticizers, pigments, antioxidants, antiozonants, a cross-linking system based either on sulphur or on sulphur and/or peroxide and/or bismaleimide donors, vulcanization accelerators, extending oils, etc. There may also be associated with the reinforcing white filler of the invention, if necessary, a conventional non-reinforcing white filler, such as clays, bentonite, talc, chalk, kaolin or titanium oxide.

The compositions according to the invention may additionally contain, covering agents (containing only the Y function) for the reinforcing white filler, such as, alkylalkoxysilanes, polyols or amines, or even coupling agents other than those mentioned above.

The compositions according to the invention may be used alone or in a blend with any other rubber composition which can be used for manufacturing tires.

II-5. Preparation of the Compositions

The rubber compositions are prepared using the diene elastomers according to techniques known to the person skilled in the art, for example by thermomechanical working in one or two stages in a internal paddle mixer, followed by mixing on an external mixer.

According to a conventional one-stage process, all the necessary constituents with the exception of the vulcanization system, are introduced into a conventional internal mixer. When the apparent density of the filler is low, it may be preferable to divide the introduction thereof into several parts. The result of this first mixing stage is then taken up on an external mixer, generally an open mill, and then the vulcanization system is added thereto. A second stage may be added in the internal mixer, essentially with the aim of subjecting the mix to complementary thermomechanical treatment.

III. EXAMPLES

III-1. Synthesis of the Aluminum-based Fillers

The synthesis of the aluminum-based fillers according to the invention which are used in the examples of embodiment below is performed according to paragraph II-2 of Section II above, using the following specific conditions below.

1) Products A, B and C (in Accordance with the Invention)

In a one-liter reactor, 150 ml (milliliters) of a solution of ammonium carbonate $(NH_4)_2CO_3$ (purity 30–33% $NH_3$, sold by Merck), of a concentration of 5.22 mol/l (moles per liter), was added in several portions to 350 ml of a solution of aluminum sulphate $Al_2(SO_4)_3 \cdot 16H_2O$ (sold by Fluka) with a concentration of 0.86 mol/l of $Al^{3+}$. The reaction was carried out under vigorous stirring (400 rpm) at a controlled temperature of 35° C. After stirring for 45 minutes, the suspension was filtered. Its final pH was approximately 10 to 11. The product was then washed with water until a pH of 8 was reached, filtered and then redispersed in 400 ml water and finally subjected to maturation for 12 hours at 23° C. The product was then filtered, quick-frozen to 18° C. and then freeze-dried (Christ Alpha 2-4 apparatus, sold by Bioblock) in accordance with the following cycle: (i) main drying at –10° C. for 12 hours at a pressure of 1.030 mbar; then (ii) final drying at 0° C. for 12 hours at a pressure of 0.001 mbar.

Starting from the precursor product thus obtained, three aluminum-based fillers in accordance with the invention were produced (products referred to as A, B and C hereafter) in the following manner:

Product A: the precursor product was dried in an oven at 125° C. for 24 hours, then calcined in air at 300° C. for 1 hour in a muffle furnace (furnace type Carbolite RHF14/8, sold by Osi), with a temperature increase ramp of 10° C./min. After calcination, for each batch of preparation, approximately 17.5 g of aluminum oxyhydroxide powder corresponding, except for the accuracy of the analysis, to the formula $Al(OH)_{1.60}O_{0.71}$ was obtained.

Product B: product B was obtained directly by baking the precursor product at 125° C. for 24 hours. Approximately 20.5 g of aluminum hydroxide powder corresponding to the formula $Al(OH)_{2.99}O_{0.07}$ was obtained, which corresponds practically to an aluminum trihydroxide.

Product C: product C was obtained by calcination of the precursor product, in air, at 500° C. for 3 hours in a tubular furnace (furnace Carbolite type CTF15/75 610, sold by Osi), with a temperature increase ramp of 10° C./min. Approximately 16.5 g of aluminum oxyhydroxide powder corresponding to the formula $Al(OH)_{1.13}O_{0.95}$ was obtained.

2) Product D (in Accordance with the Invention)

The precursor of product D was prepared as indicated above for the precursor product of the fillers A, B and C, with the exception that the aluminum sulphate was replaced by aluminum nitrate $Al(NO_3)_3,9H_2O$ (sold by Fluka). Product D was obtained by calcination of this precursor in air at 400° C. for 2 hours in a muffle furnace (furnace type Carbolite RHF14/8, sold by Osi) with a temperature increase ramp of 10° C./min. Approximately 16 g of aluminum oxyhydroxide powder corresponding to the formula $Al(OH)_{1.02}O_{0.99}$ was obtained.

3) Product E (in Accordance with the Invention)

The synthesis was identical to that of products A, B and C above, but with the following differences. After the maturation stage for the product (12 hours at 23° C.), the volume of suspension is brought to 750 ml. The suspension was then sprayed (Büchi apparatus—"mini-spray-dryer" B-191—sold by Bioblock) under the following conditions: temperature 200° C., intake 90%, pump 20%. After spray-drying, the product was calcined in air at 200° C. for 3 hours in a muffle furnace (furnace type Carbolite RHF14/8), with a temperature increase ramp of 10° C./min. Approximately 16.5 g of aluminum oxyhydroxide powder corresponding to the formula $Al(OH)_{1.73}O_{0.63}$ was obtained.

4) Product F (Not in Accordance with the Invention)

The precursor of product F was prepared as indicated above for the precursors of the fillers A, B and C, except that, after the stage of maturation for 12 hours at 23° C., the procedure was as follows: The product was then filtered and placed in a vacuum oven at 80° C. for 24 hours. The dried product was crushed slightly in a mortar, then placed in the oven for 18 hours at 125° C. and 6 hours at 140° C. Approximately 18 g of product corresponding to the formula $Al(OH)_{1.88}O_{0.56}$ was obtained.

It will be noted that this product is prepared using a process which is not in accordance with the invention, since stage (iii) of drying of the filtrate was performed roughly in a vacuum oven at 80° C. for 24 hours without using a specific drying method, such as cryogenic freeze-drying, capable of limiting the agglomeration of the hydroxide particles by capillarity when the water was eliminated.

5) Product G (in Accordance with the Invention)

The synthesis was identical to that of products A, B and C, except for the difference that the precursor was calcined in air at 200° C. for 3 hours in a muffle furnace (Carbolite RHF14/8), with a temperature increase ramp of 10° C./min. Approximately 17 g of a product corresponding to the formula $Al(OH)_{1.52}O_{0.74}$ was obtained.

6) Product H (Not in Accordance with the Invention)

This is an aluminum hydroxide $Al(OH)_3$ sold by Riedel-de-Haen (reference: 11033).

7) Product I (Not in Accordance with the Invention)

This product was prepared by a conventional sol-gel method such as described, for example, in "Sol-Gel Science", C. J. Brinker, G. W. Scherer, Academic Press 1990. It corresponds to the formula $Al(OH)_{1.63}O_{0.69}$.

The characteristics of products A to I thus obtained are set forth in Table 1.

Products F, H and I are not in accordance with the invention for the following reasons: product F has too high a size $d_w$ and too low a rate $\alpha$; product H has characteristics of BET surface area, of size $d_w$ and of rate $\alpha$ which are all outside the recommended ranges; product I has too high a size $d_w$.

Products A, B, C, D, E and G are all in accordance with the invention; they have in particular a disagglomeration rate $\alpha$ greater than the set lower limit of $5\times10^{-3}$ $\mu m^{-1}/s$ (or $\frac{2}{3}$ of $\alpha_0$).

The rates $\alpha$ measured on the products in accordance with the invention must be considered to be particularly high, since the ultrasound disagglomeration test applied to a highly dispersible control silica (Zeosil 1165MP, sold by Rhône-Poulenc) results in a rate $\alpha$ of approximately $7.5\times10^{-3}$ $\mu m^{-1}/s$ (referred to as $\alpha_0$), or a rate which is intermediate between those measured on product E (approximately 75% of ($\alpha_0$), products C and D (approximately 90% of $\alpha_0$) and those measured on products A (approximately 130% of $\alpha_0$), B (approximately 140% of $\alpha_0$) and G (approximately 160% of $\alpha_0$). Note that in accordance with a preferred embodiment of the invention, the disagglomeration rate $\alpha$ measured on the majority of the products according to the invention is greater than $6\times10^{-3}$ $\mu m^{-1}/s$ (i.e. 80% of $\alpha_0$), at least equal to $\alpha_0$ for products A, B and G.

X-ray diffraction analysis furthermore revealed that products A, B, E and G have an amorphous structure (a simple diffuse halo on a powder diffractogram), whereas products C and D have a very poorly crystallised, virtually amorphous structure (a few diffraction rings poorly defined).

II-2. Preparation of the Compositions

The compositions tested hereafter were prepared in known manner in laboratory mixers as follows: The diene elastomer was introduced into an internal mixer filled to 75%, the temperature of which was approximately 70° C. After a suitable kneading time, for example of the order of 1 minute, all the other ingredients, with the exception of the vlucanization system were added, including the filler (in one or more portions) and if applicable the associated coupling agent. Thermomechanical working of a duration of about 12 minutes was then performed, with an average blade speed of 70 rpm, until a dropping temperature of about 140° C. was obtained. The mixture thus obtained was recovered, then the vulcanization system was added on an external mixer (homo-finisher) at 30° C. The vulcanization was carried out at 150° C.

III-3. Tests

1) Series 1 (Compositions No. 1 to No. 5)

Five diene rubber compositions intended for the manufacture of tires or treads for tires are compared below. The SBR elastomer (styrene-butadiene copolymer) is an SBR prepared in solution, and comprises 25% styrene, 58% 1,2-polybutadiene bonds and 23% polybutadiene trans-1,4 bonds.

The five compositions are generally identical, apart from the following differences in filler:

composition No. 1: conventional reinforcing filler (black filler) constituted by an N234-type carbon black;

composition No. 2: reinforcing white filler constituted by a highly dispersible silica (Rhône-Poulenc silica Zeosil 1165MP);

composition No. 3: reinforcing white filler constituted by product A;

composition No. 4: reinforcing white filler constituted by product B;

composition No. 5: white filler constituted by product H.

For each composition, the amount of filler (whether reinforcing or not) was adjusted, according to density, so as to keep the volume percentage of this filler constant. Furthermore, the coupling agent Si69 was introduced at a rate corresponding to identical surface covering for the silica and products A and B, namely an amount of about $9.3\times10^{-7}$ mole/m² of reinforcing white filler, except for product H, the very low BET surface area of which inevitably resulted in the use of a great excess of coupling agent.

Only compositions No. 3 and No. 4 are in accordance with the invention. Tables 2 and 3 show in succession the formulation of the different compositions (Table 2—amount of the different products expressed in phr), and their properties before and after curing at 150° C. for 40 minutes (Table 3). FIG. 1 shows the curves of modulus (in MPa) as a function of the elongation (in %); these curves are marked C1 to C5, and correspond to compositions No. 1 to No. 5, respectively.

A study of these various results leads to the following observations:

The Mooney plasticity values are sufficiently low and relatively close for compositions No. 1 to No. 4, which reveals for each a good ability to be in the cured state.

The compositions according to the invention (No. 3 and No. 4) have moduli M100 and M300, which indicate to the person skilled in the art the quality of reinforcement, which is greater than those obtained on the control compositions No. 1 (carbon black) and No. 2 (silica), which make it possible to predict wear resistance which is particularly advantageous for tire treads comprising such a composition according to the invention. The values of modulus are extremely low for composition No. 5, which is not in accordance with the invention (filler H).

FIG. 1 confirms the above observations: composition No. 3 (curve C3) reveals a reinforcement performance which is equivalent at low elongation, then greater at higher elongations, compared with those of composition No. 1 (carbon black; curve C1) and of composition No. 2 (silica; curve C2). Composition No. 4 (curve C4) shows a performance which is substantially equivalent to that of the known reinforcing fillers (silica and carbon black). Composition No. 5 (curve C5), shows that the filler H which is not in accordance with the invention, is not a reinforcing filler.

The amount of coupling between filler and elastomer (illustrated by the so-called "bound rubber" test) obtained with filler A appears to be not only greater than that obtained with the siliceous filler, but even greater than that obtained with the conventional black filler. The amount of coupling for filler B is also very satisfactory, since it lies between those observed with silica and carbon black. Measurement of "bound rubber" was impossible for composition No. 5 owing to disintegration (insufficient cohesion) of the latter (product H not in accordance with the invention).

It is further noted that the compositions according to the invention (No. 3 and No. 4) have very advantageous hysteretic properties, compared, in particular, with those offered by the highly dispersible silica, with a very significant reduction in the losses by rebound (HL), in the non-linearity $\Delta G^*$ and in $\tan(\delta)_{max}$, which makes it possible to predict particularly low rolling resistance for tire treads comprising such a composition according to the invention.

Finally, it is noted that filler A of composition No. 3 (a<3 in formula (I) aluminum oxyhydroxide), compared with filler B of composition No. 4 (a=3 in formula (I)—aluminum tri-hydroxide), offers superior performance: higher moduli M100 and M300 (greater reinforcement), greater amount of coupling filler/elastomer ("bound rubber").

2) Series 2 (Compositions No. 6 to No. 9)

Four other diene rubber compositions also intended for the manufacture of tires or treads for tires are compared below. The SBR elastomer is identical to that used for the preceding compositions.

These four compositions are identical, apart from the following differences in filler:
composition No. 6: N234-type carbon black;
composition No. 7: Rhône-Poulenc silica Zeosil 1165MP;
composition No. 8: reinforcing white filler constituted by product C;
composition No. 9: white filler constituted by product I.

As above, the amount of filler (whether reinforcing or not) in the composition has been adjusted, according to density, so as to keep the volume percentage of this filler constant. Furthermore, the coupling agent Si69 was introduced at a rate corresponding to identical surface covering for all the white fillers, namely an amount of about $9.3 \times 10^{-7}$ mole/$m^2$ of white filler.

Figure 2:
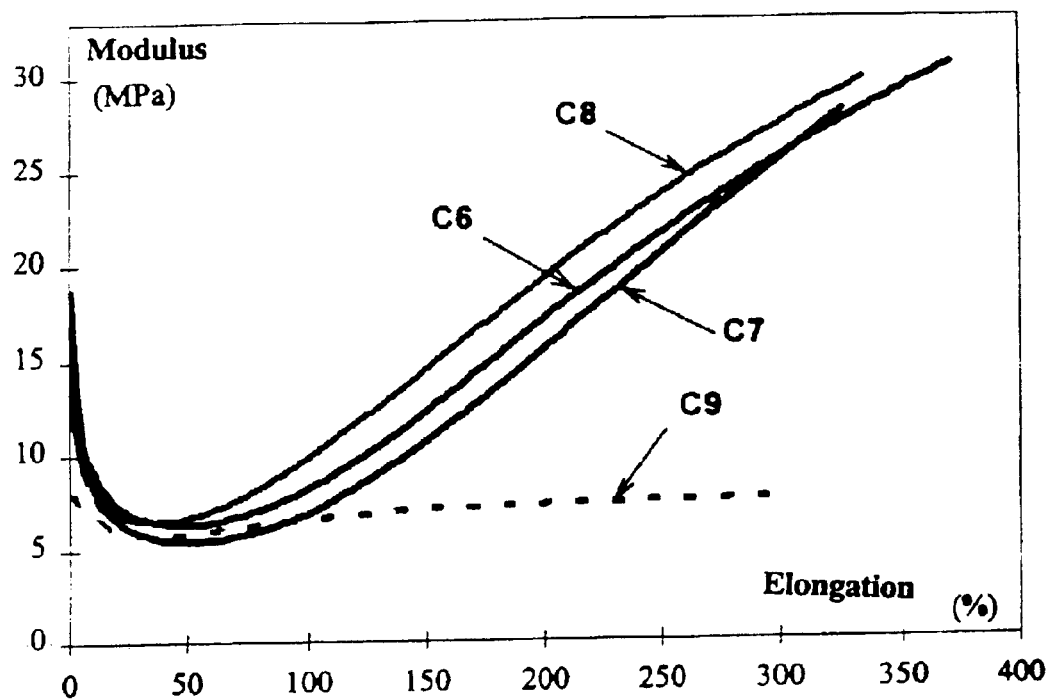

Only composition No. 8 is in accordance with the invention. Tables 4 and 5 show in succession the formulation of the different compositions (Table 4—amount of the different products expressed in phr), and their properties before and after curing at 150° C. for 40 minutes (Table 5). The values of moduli M10, M100 and M300 indicated in Table 5 have been measured here in a first elongation (i.e. without an accommodation cycle). FIG. 2 shows the curves of modulus (in MPa) as a function of the elongation (in %). The curves marked C6 to C9 correspond to compositions No. 6 to No. 9 respectively.

A study of these various results leads to the following observations:

The composition according to the invention (No. 8) has moduli M100 and M300 which are greater than those obtained on the control compositions No. 6 (carbon black) and No. 7 (silica), which make it possible to predict wear resistance which is particularly advantageous for tire treads comprising such a composition according to the invention.

FIG. 2 confirms the previous observations: Composition No. 8 (curve C8) according to the invention reveals a reinforcement performance which is equivalent at low elongation, then rapidly greater at higher elongations, compared with those of composition No. 6 (carbon black; curve C6) and of composition No. 7 (silica; curve C7).

The amount of coupling between filler and elastomer ("bound rubber") obtained with filler C of the invention (composition No. 8) is not only greater than that obtained with the siliceous filler, but even greater than that obtained with the conventional black filler.

Finally, as far as composition No. 9 is concerned, which is based on an aluminous filler not in accordance with the invention, the values of the moduli M100 and M300 (Table 5) are extremely low, which is a sign of non-existent reinforcement, as is also illustrated by the curve C9 of FIG. 2. This correlates well to the result of the "bound rubber" test (measurement impossible owing to disintegration—insufficient cohesion—of composition No. 9); clearly, product I is not a reinforcing filler.

Thus, unexpectedly, the aluminum-based fillers according to the invention have a performance which is superior in the majority of cases to that of a highly dispersible precipitated silica, for the same proportion by volume of white filler.

A reading of FIGS. 1 and 2 shows that:
The best results (curves C3 and C8) obtained for compositions according to the invention are superior to those observed with compositions of the prior art reinforced with carbon black (curves C1 or C6) or with a highly dispersible precipitated silica (curves C2 or C7).

These very good results of curves C3 and C8 correspond to the compositions reinforced by oxyhydroxides (a<3), more specifically, oxyhydroxides satisfying the preferred relationship a<2.

The results obtained with the tri-hydroxides (a=3) are nevertheless entirely satisfactory when compared to those obtained with the fillers of the prior art (compare curve C4 to curves C1 and C2 of FIG. 1).

Due to their specific morphological properties, the aluminum-based fillers according to the invention thus offer an entirely advantageous alternative to the use of highly dispersible silicas.

The compositions of the invention are thus able to impart, in particular to treads for tires, not only the usual properties provided by white fillers, that is to say, low rolling resistance and improved grip to dry, wet or snow-covered ground, but also wear resistance which is at least equal to that obtained with compositions filled conventionally with a carbon black.

IV. Device and Method According to the Invention

The ultrasound disagglomeration test described in paragraph I-1-c and used for characterizing the fillers A to I described in the above examples of Section III constitutes the direct application of a measuring method and device which constitute other subjects of the present invention.

It should be noted that the method and the device of the invention which are described hereafter apply to any type of filler, whether reinforcing or not. In particular, they are not limited to the reinforcing aluminum-based filler described previously; nor are they limited to the case of fillers intended to reinforce rubber compositions.

IV-1. Method of the Invention

The subject of the invention is a method for measuring the ultrasound disagglomeration rate of a filler in the form of agglomerates of particles, by continuously measuring the evolution of the size of these agglomerates during an operation to break up these agglomerates, in particular by ultrasound generation.

The method of the invention comprises:

(a) introducing the filler into a liquid so as to form a homogenous liquid suspension;

(b) circulating this liquid suspension in the form of a flow through a circuit comprising breaking means which, as the flow passes, break up the agglomerates, and a laser granulometer which, at regular intervals of time "t", measures the size "d" of these agglomerates;

(c) recording the evolution of the size "d" as a function of the time "t"; such that (d) the disagglomeration rate or a parameter linked to this rate is deduced therefrom.

"Size" d of agglomerates is understood to mean any size parameter which can be deduced from the size distribution in volume which can be measured by the laser granulometer, be it, the size distribution itself, a mode of distribution, the average size, the median size or any other indicator of size. These different parameters may be determined for all or only part of the agglomerates (for example for a given size class) present in the suspension of filler which is analyzed.

Preferably, the size parameter used is the average size by volume of the agglomerates (of all the agglomerates), referred to as $d_v$ in the present application, in accordance, for example, with the ultrasound disagglomeration test. In this case, the disagglomeration rate, referred to as "α", is represented by the gradient of the straight line $[1/d_v(t)=f(t)]$ recorded by the measurement chain of the granulometer, in a zone of steady state conditions of disagglomeration.

The liquid used may be any liquid capable of forming a liquid suspension of the filler tested. Water may be used, or any liquid which is more appropriate to the particular case in question, for example directly the liquid matrix for which the filler tested is intended, if applicable. The water may optionally have a surfactant added to it so as to stabilize the suspension. This surfactant may be anionic, cationic or neutral (e.g. non-ionic), depending on the nature of the filler.

The concentration of filler in the liquid suspension may vary within a wide range, depending on the nature of the filler to be studied and its optical properties. To characterize reinforcing fillers which can be used in rubber compositions for tires, for example, this concentration may vary, for example, between 0.001 and 10 grams of filler per liter of liquid. It will be adjusted empirically so as to obtain a signal which can be used throughout the breaking operation. Generally, the concentration used is greater when the refractive index is closer to that of the suspension liquid (for example, silicas relative to water). It is lower when the refractive index is farther away (for example, carbon blacks relative to water).

The temperature of the suspension may be room temperature (about 20° C.) or a different temperature, for example the real temperature used when dispersing the filler in its application matrix.

The flow of liquid suspension in the measuring circuit is circulated at a controlled, constant rate during the entire measurement. A rate of the order of a liter or several liters per minute is generally sufficient to effect a measurement of "d" which is statistically satisfactory. This rate can be adjusted according to the particular conditions of implementation of the invention.

Prior measurement of the background noise is carried out by circulating the suspension liquid alone in the circuit before introducing the filler to be tested into said liquid.

After a sufficient number of measurements "d", the disagglomeration rate (or other parameter linked to this rate) may be deduced from the gradient of the straight line $[1/d(t)=f(t)]$ recorded by the measurement chain of the granulometer, in a zone of steady state conditions of disagglomeration. It is also possible to use any other parameter linked to the disagglomeration rate which can provide a discrimination criterion for selecting fillers, in particular reinforcing fillers for rubber compositions for tires.

The person skilled in the art will be able to implement the method of the invention with different breaking means suitable for continuous disagglomeration of the agglomerates of particles of the filler to be tested, in the suspension liquid. By way of example, reference is made to an ultrasonic probe or tank, mechanical breaking means such as, for example, a homogenizer or any other suitable dispersion means.

The invention is preferably carried out using an ultrasonic probe. One particular example of implementation of the method of the invention is illustrated by the ultrasound disagglomeration test described in paragraph I-1-c above and used for characterizing the fillers A to I, described in the examples of Section III above.

Figure 4:
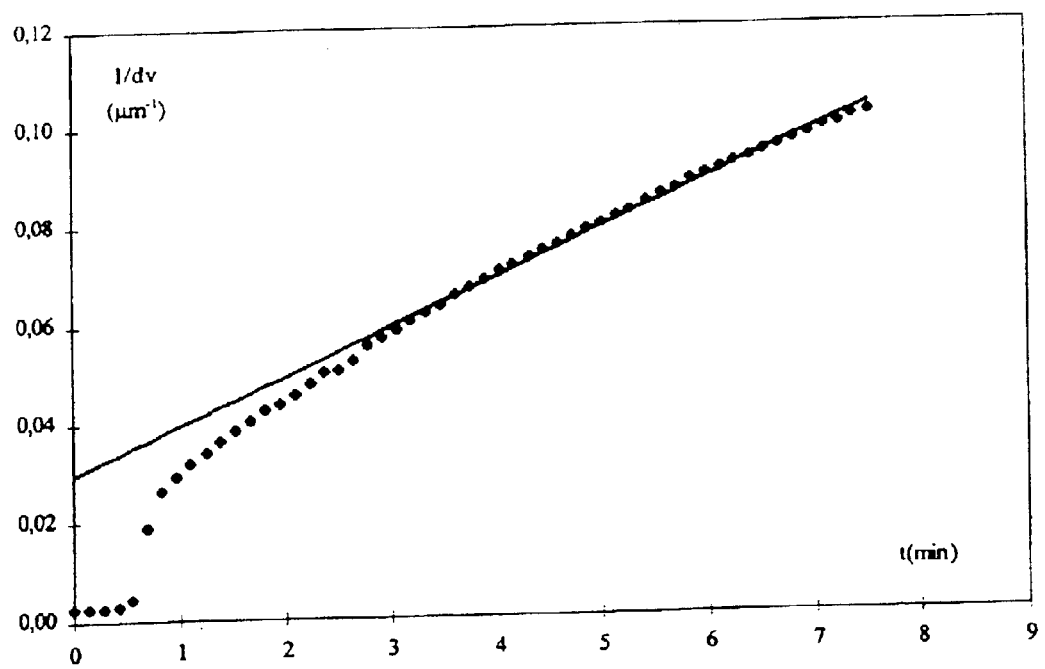
FIG. 4 is a curve of the change in the size of the agglomerates during ultrasound generation, obtained from the device of FIG. 3, from which curve the disagglomeration rate α is determined.

By way of example, FIG. 4 reproduces the curve $[1/d_v(t)=f(t)]$ recorded for the filler A under the specific conditions of this disagglomeration test. It can clearly be seen from FIG. 4 that the first points recorded ("t" varying from 0 to about 30 s) correspond to the measurement of the initial diameter $d_v[0]$, followed (after actuation of the ultrasonic probe) by progressive passage (here, "t" from 30 s to about 3 min) to steady state conditions of disagglomeration during which the reciprocal of "$d_v$" does vary linearly with the time "t". The recording of the data is stopped here after about 8 minutes. The disagglomeration rate α ($9.8 \times 10^{-3}$ $\mu m^{-1}/s$) in the zone of steady state conditions of disagglomeration is deduced from this by calculation of linear regression, performed by the calculator of the granulometer.

The measurement method of the invention is preferably implemented using a measuring device as described below.

IV-2. Device of the Invention

The above method may be carried out using a novel device, which constitutes another subject of the invention.

This device of the invention, having a circuit within which a flow of agglomerates of particles suspended in a liquid can circulate, comprises:

(i) a sample preparer, intended to receive the sample of filler to be tested and to send it through the circuit in the form of said flow;

(ii) a laser granulometer intended to measure the size of the agglomerates as the flow passes;

(iii) a treatment cell provided with breaking means for breaking up the agglomerates as the flow passes:

(iv) at least one vent to the open air for removing air bubbles resulting from the breaking operation.

Examples of breaking means suitable for disagglomerating the suspended agglomerates include an ultrasonic probe placed in the treatment cell, an ultrasound tank surrounding the treatment cell, or mechanical breaking means such as, for example, a homogenizer or other suitable dispersion means. Preferably an ultrasonic probe placed in the treatment cell is used.

Figure 3:
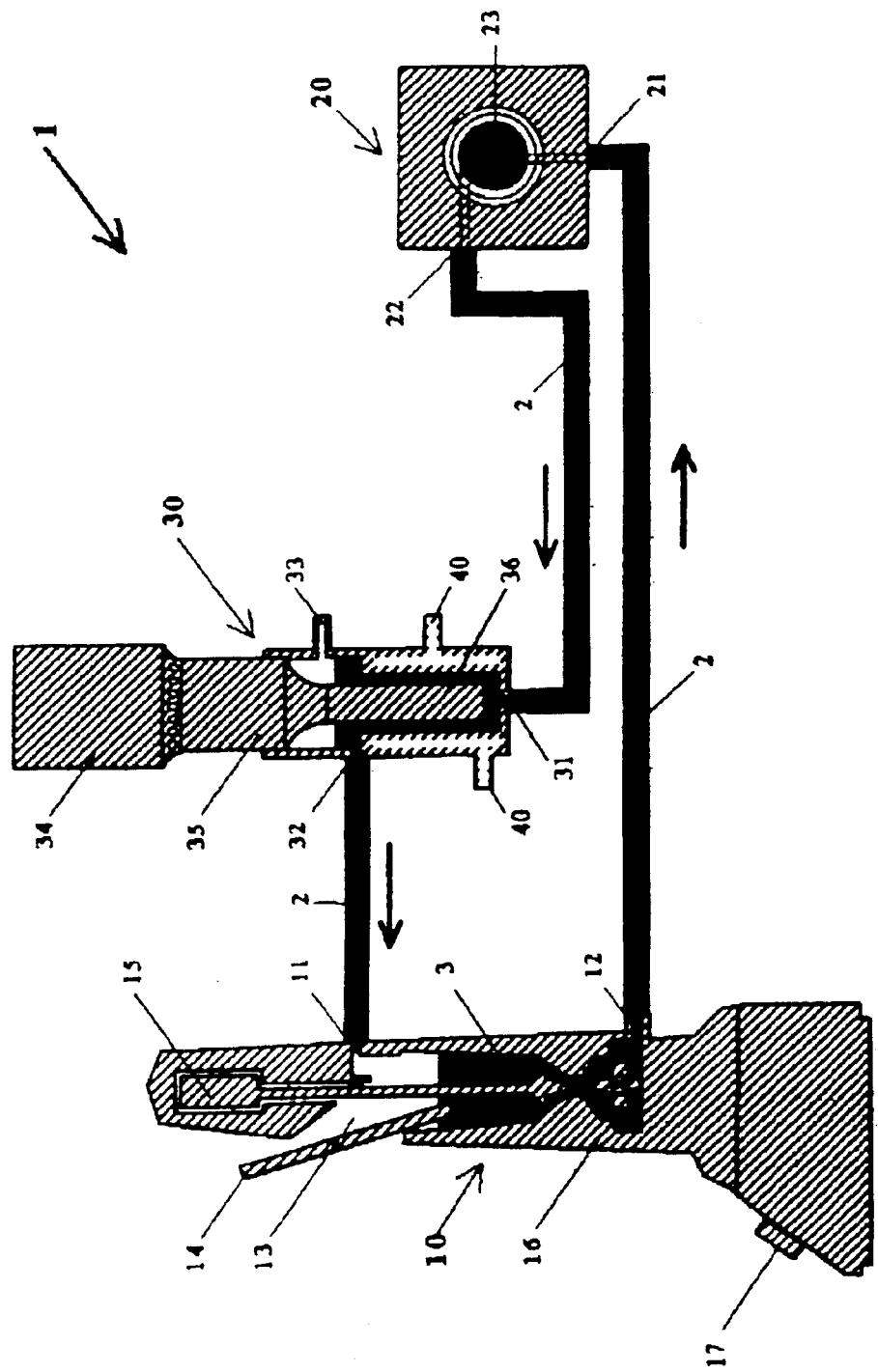
FIG. 3 is a diagram of a device suitable for measuring the ultrasound disagglomeration rate of a filler in the form of agglomerates.

An example of a measuring device according to the invention is illustrated in FIG. 3 which consists of a closed circuit 1 within which a flow 2 of agglomerates of particles suspended in a liquid 3 can circulate. This device comprises a sample preparer 10, a laser granulometer 20 and a treatment cell 30 provided with an ultrasonic probe 35, the detailed description of which follows.

a) Sample Preparer

The sample preparer 10 is intended to receive the sample of filler to be tested (as it is, or already in suspension in the liquid 3) and to send it through the circuit 1 at a controlled speed (potentiometer 17), in the form of a flow 2 of liquid suspension.

Preparer 10 consists of a tank which contains, and through which circulates, the suspension to be analyzed; in order to prevent sedimentation of the agglomerates of particles of the suspension, provision is made for continuous stirring by means of a motor 15 of variable speed. A centrifugal mini-pump 16 is intended to circulate the suspension 2 in the circuit 1. The entrance 11 to the preparer 10 is connected to the open air by an opening 13 intended to receive the sample of filler to be tested and/or the liquid 3 used for the suspension.

To implement the invention, a sample preparer such as the "Malvern Small Sample Unit MSX1", sold by Malvern Instruments, is used.

b) Laser Granulometer

A laser granulometer 20, which continuously measures at regular time intervals, the size d of the agglomerates as the flow 2 passes, by means of a measuring cell 23 to which are coupled the automatic recording and calculation means of the granulometer 20, is connected to the preparer.

Laser granulometers utilize, in known manner, the principle of diffraction of light by solid objects suspended in a medium, the refractive index of which differs from that of the solid. According to the theory of Fraunhofer, there is a relationship between the size of the objects and the angle of diffraction of light (the smaller the object, the greater the angle of diffraction). In practice, it is sufficient to measure the amount of light diffracted for different angles of diffraction to be able to determine the size distribution (by volume) of the sample, from which there is determined, for example, the size $d_v$ corresponding to the mean of this distribution ($d_v = \Sigma(n_i d_i^4)/\Sigma(n_i d_i^3)$ where $n_i$=number of objects of the size class $d_i$).

Laser granulometers and the principle of operation thereof have been described, for example, in EP-A-0 465 205, EP-A-0 559 529, FR-A-2 713 773 and GB-A-2 203 542.

To implement the invention, the laser granulometer "Mastersizer S", sold by Malvern Instruments, equipped with an He—Ne red laser source (wavelength 632.8 nm) is used.

c) Treatment Cell

The treatment cell 30 equipped with an ultrasonic probe 35 (converter 34 and probe head 36) intended continuously to break up the agglomerates of particles as the flow 2 passes is inserted between the preparer 10 and the laser granulometer 20.

According to a preferred embodiment of the invention, the treatment cell 30 is arranged between the outlet 22 from the granulometer 20 and the inlet 11 to the preparer 10, such that, in operation, the flow 2 of agglomerates of particles emerging from the preparer 10 passes through the laser granulometer 20 before entering the treatment cell 30. This arrangement has two major advantages for measurements: First, the air bubbles resulting from ultrasound generation (action of the ultrasonic probe) are eliminated on passing through the preparer 10 (which is in the open air), that is to say, before entering the granulometer 20; they therefore do not upset the laser diffraction measurement. Second, the homogeneity of the suspension is improved by first passing through the preparer 10.

According to another preferred embodiment of the invention, the treatment cell 30 is arranged such that, during operation, the flow 2 of particles which penetrates therein, via an inlet 31, first passes in front of the head 36 of the ultrasonic probe 35. Thus, the treatment cell 30 shown in FIG. 3 is used unconventionally: the flow 2 enters through the bottom 31 of the cell (and not through the top 32), which is contrary to the maker's recommendations. This configuration nevertheless has two major advantages for the measurement of the disagglomeration rate: First, all the circulating suspension 2 is forced to pass in front of the end 36 of the ultrasonic probe 35, which is the zone most active in terms of disagglomeration; second, this arrangement permits initial degasification after ultrasound generation in the body of the treatment cell 30 itself, the surface of the suspension 2 then being in contact with the atmosphere by means of a pipe 33 of small diameter.

The power of the ultrasonic probe 35 (more generally of the breaking means) is adjusted according to the nature of the filler to be studied and the disagglomeration rates expected for this type of filler, so as to be able to perform the complete cycle of measurements of "d" which is necessary to determine the disagglomeration rate, in a reasonable time, for example about 10 minutes (for example, recording of a measurement of "d" about every 10 seconds).

To characterize reinforcing fillers intended for rubber compositions for tires, preferably an ultrasonic probe is used, the output of which lies within a range from 10 to 2000 W. It has been noted that a power of 10–20 W is sufficient for certain carbon blacks, whereas powers from 300 to 1000 W are more suitable for certain white fillers such as siliceous or aluminous fillers which, in known manner, are more difficult to disperse owing to greater interactions between particles (aggregates). Obviously, the results obtained with different outputs of ultrasound generation cannot be compared directly.

To implement the invention, a treatment cell of the type "M72410" provided with an ultrasonic probe (ultrasound generator type "Vibracell ½ inch") of a maximum power of 600 W, both sold by Bioblock, is used.

d) Other Elements

In the device according to the invention, at least one vent to the open air is used to permit continuous elimination of the air bubbles which form during ultrasound generation (more generally during the breaking operation). Such vents to atmospheric pressure (13, 33) are shown in FIG. 3, at the level of the sample preparer 10 and of the treatment cell 30 itself.

Although not essential, it is preferred that the flow 2 be thermostatically controlled, for example by means of a cooling circuit 40 arranged, at the level of the cell 30, in a double casing surrounding the probe 35, the temperature being controlled, for example, by a heat sensor 14 immersed in the liquid 3 at the level of the preparer 10.

The arrangement of the various elements of the measuring device is finally optimized so as to restrict as far as possible the circulating volume, i.e., the length of the connecting tubes (for example, flexible tubes). The total volume of liquid suspension is that necessary to fill the circuit 1 (preferably less than 200 ml, for example 160 ml for the disagglomeration test described in paragraph I-1-c above).

ing fillers, in particular reinforcing fillers for rubber compositions for tires.

There was very good correlation between the disagglomeration rate measured in accordance with the method of the invention and the dispersibility of a filler, i.e., its ability to disperse in a given matrix.

It will be recalled that the reinforcing ability of a filler, relative to a rubber matrix, is closely correlated to its dispersibility. In other words, the measurement of the disagglomeration rate in accordance with the claimed method, associated with the measurements of the BET surface areas and size $d_w$ of the particles, makes it possible a priori to evaluate the reinforcing potential of different fillers, and to be able to classify them rapidly, without it being necessary to manufacture rubber compositions, to incorporate the fillers therein and then to test the compositions thus filled mechanically.

The person skilled in the art of fillers, whether reinforcing ones or not, will comprehend the major advantage of the method and the device of the invention for a large number of applications other than the tire rubber manufacturing industry, for example for the in situ characterization of a filler placed directly in suspension in the matrix for which it is intended, when this matrix is liquid.

TABLE 1

| Product: | A | B | C | D | E | F | G | H | I |
|---|---|---|---|---|---|---|---|---|---|
| $H_2O$ (%) | 5.1 | 6.0 | 6.0 | 5.20 | 6.5 | 5.50 | 5.10 | 0.20 | 12.9 |
| Oxygen (%) | 55.40 | 60.24 | 53.19 | 55.00 | 57.43 | 58.58 | 56.03 | 61.94 | 60.38 |
| Aluminum (%) | 37.10 | 30.25 | 38.70 | 42.20 | 36.70 | 37.07 | 38.30 | 34.18 | 35.38 |
| Hydrogen (%) | 2.79 | 4.05 | 2.31 | 2.19 | 3.10 | 3.22 | 2.75 | 3.88 | 3.60 |
| He Density (g/ml) | 2.46 | 2.33 | 2.55 | 2.55 | 2.41 | 2.59 | 2.34 | 2.41 | 2.32 |
| BET (m$^2$/g) | 281 | 222 | 149 | 298 | 138 | 336 | 174 | 1 | 198 |
| $d_w$ (nm) | 127 | 129 | 126 | 82 | 188 | 39550 | 88 | 8790 | 2830 |
| α ($\mu$m$^{-1}$/s) | 0.0098 | 0.0107 | 0.0068 | 0.0069 | 0.0057 | 0.0013 | 0.0118 | 0.0031 | 0.0072 | e) Automation of the Measurements

Automation of the measurement, calculation and saving of the results was effected by means of the language Basic Malvern available on the command program of the "Mastersizer S" granulometer referred to above. This automation involved carrying out the following operations:

- acquisition of the identification of the product;
- alignment of the lens system of the laser;
- measurement of the background noise;
- introduction of the sample of filler (fine powder) into the preparer;
- starting of the measurement cycle once the obscuration of the signal of the beam exceeds 1% (i.e. less than 99% transmission);
- performance of 70 cycles (measurement, calculation of the size distribution (in volume), saving the distribution, the time elapsed and the average diameter by volume $d_v$);
- automatic calculation of α;
- recording of all the data;
- stop.

IV-3. Evaluation of the Dispersibility of a Filler

The method and the device of the invention which are described above are advantageously used to evaluate the intrinsic dispersibility of a filler and the disagglomeration rate (or any other parameter linked to this rate), which are advantageously used as a discrimination criteria for select-

TABLE 2

| Composition No.: | 1 | 2 | 3 | 4 | 5 |
|---|---|---|---|---|---|
| SBR (1) | 100 | 100 | 100 | 100 | 100 |
| Carbon black (2) | 50 | — | — | — | — |
| Silica (3) | — | 52.5 | — | — | — |
| Product A | — | — | 61.5 | — | — |
| Product B | — | — | — | 58.3 | — |
| Product H | — | — | — | — | 60.3 |
| Si69 (4) | — | 4.2 | 8.65 | 6.5 | 3.3 |
| ZnO | 2.5 | 2.5 | 2.5 | 2.5 | 2.5 |
| Stearic acid | 2 | 2 | 2 | 2 | 2 |
| Antioxidant (5) | 1.9 | 1.9 | 1.9 | 1.9 | 1.9 |
| DPG (6) | 1.5 | 1.5 | 1.5 | 1.5 | 1.5 |
| Sulphur | 1 | 1 | 1 | 1 | 1 |
| CBS (7) | 2 | 2 | 2 | 2 | 2 |

(1) butadiene-styrene copolymer
(2) type N234
(3) Zeosil 1165 MP (Rhône-Poulenc)
(4) bis(triethoxysilylpropyl)tetrasulphide
(5) N-1,3-dimethylbutyl-N-phenyl-paraphenylenediamine
(6) Diphenylguanidine
(7) N-cyclohexyl-2-benzothiazylsulphenamide

TABLE 3

| Composition No.: | 1 | 2 | 3 | 4 | 5 |
|---|---|---|---|---|---|
| Plasticity (MU) | 61 | 52 | 76 | 51 | 27 |
| Bound Rubber (%) | 33 | 24 | 36 | 28 | — |

TABLE 3-continued

| Composition No.: | 1 | 2 | 3 | 4 | 5 |
|---|---|---|---|---|---|
| M10 (MPa) | 6.52 | 6.09 | 6.39 | 5.76 | 3.24 |
| M100 (MPa) | 4.87 | 5.07 | 6.80 | 6.2 | 2.37 |
| M300 (MPa) | 12.13 | 13.29 | 15.35 | 14.04 | 2.53 |
| HL (%) | 36.4 | 22.5 | 18.3 | 15.2 | 11.8 |
| $\Delta G^*$ (MPa) | 5.58 | 2.34 | 1.47 | 0.81 | 0.25 |
| $\tan(\delta)_{max}$ | 0.343 | 0.247 | 0.218 | 0.202 | 0.154 |

TABLE 4

| Composition No.: | 6 | 7 | 8 | 9 |
|---|---|---|---|---|
| SBR (1) | 100 | 100 | 100 | 100 |
| Carbon black (2) | 50 | — | — | — |
| Silica (3) | — | 52.5 | — | — |
| Product C | — | — | 63.8 | — |
| Product I | — | — | — | 58 |
| Si69 (4) | — | 4.2 | 4.75 | 5.7 |
| ZnO | 2.5 | 2.5 | 2.5 | 2.5 |
| Stearic acid | 2 | 2 | 2 | 2 |
| Antioxidant (5) | 1.9 | 1.9 | 1.9 | 1.9 |
| DPG (6) | 1.5 | 1.5 | 1.5 | 1.5 |
| Sulphur | 1.5 | 1.5 | 1.5 | 1.5 |
| CBS (7) | 2.5 | 2.5 | 2.5 | 2.5 |

(1) idem Table 2; (2) idem table 2;
(3) idem Table 2; (4) idem Table 2;
(5) idem Table 2; (6) idem Table 2;
(7) idem Table 2.

TABLE 5

| Composition No.: | 6 | 7 | 8 | 9 |
|---|---|---|---|---|
| Bound Rubber (%) | 29 | 28 | 35 | — |
| M10 (MPa) | 9.28 | 7.08 | 8.30 | 6.83 |
| M100 (MPa) | 8.18 | 6.90 | 9.82 | 6.59 |
| M300 (MPa) | 25.55 | 25.44 | 27.34 | 7.57 |

What is claimed is:

1. A device for measuring an ultrasound disagglomeration rate of a filler in the form of agglomerates of particles, said device comprising a circuit (1) within which a flow (2) of the particles suspended in a liquid (3) can circulate, and at least:
   (i) a sample preparer (10), intended to receive a sample of filler to be tested and to send it through the circuit (1) in the form of the flow (2);
   (ii) a laser granulometer intended to measure the size of the agglomerates as the flow passes; and
   (iii) a treatment cell (30) provided with breaking means (35) for breaking up the agglomerates as the flow (2) passes;
   (iv) at least one vent to the open air (13, 33) for removing air bubbles due to the breaking operation.

2. A measuring device according to claim 1, wherein the breaking means is an ultrasonic probe (35).

3. The device of claim 1, wherein the continuous treatment cell (30) is arranged between the outlet (22) of the granulometer (20) and the inlet (11) of the preparer (10), such that the flow (2) of particles emerging from the preparer (10) passes through the laser granulometer (20) before entering the treatment cell (30).

4. The device of claim 2, wherein the treatment cell (30) is arranged such that the flow (2) of particles which penetrates into said cell (30), via an inlet (31), passes in front of the head (36) of the ultrasonic probe (35).

5. The device of claim 2, wherein the ultrasonic probe (35) has a power within a range from 10 to 2000 watts.

6. A method for measuring an ultrasound disagglomeration rate of a filler in the form of agglomerates of particles, comprising:
   (a) introducing the filler into a liquid so as to form a homogenous liquid suspension;
   (b) circulating the liquid suspension in the form of a flow through a circuit comprising breaking means which, as the flow passes, break up the agglomerates, and a laser granulometer which, at regular intervals of time "t", measures the size "d" of these agglomerates;
   (c) recording the evolution of the size "d" as a function of the time "t"; wherein
   (d) the disagglomeration rate or a parameter linked to this rate is deduced therefrom.

7. The method of claim 6, wherein the size measured is the average size in volume of the agglomerates of particles, referred to as $d_v$, the disagglomer-ation rate, "$\alpha$", being represented by the gradient of the straight line $[1/d_v(t)=f(t)]$ observed in a zone of steady state conditions of disagglomeration.

8. The method of claim 6, wherein the breaking means is an ultrasonic probe.

* * * * *